United States Patent [19]
D'Amelio et al.

[11] Patent Number: 4,699,463
[45] Date of Patent: Oct. 13, 1987

[54] MULTIDIRECTIONAL VIEWING BORESCOPE

[75] Inventors: Frank D. D'Amelio, Naugatuck, Conn.; Dominick G. Esposito, Mamaroneck; Walter B. Kobyra, Bronx, both of N.Y.

[73] Assignee: Circon Corporation, Santa Barbara, Calif.

[21] Appl. No.: 794,491

[22] Filed: Nov. 1, 1985

[51] Int. Cl.⁴ .............................................. G02B 6/06
[52] U.S. Cl. .................................... 350/96.26; 128/4
[58] Field of Search ............. 350/96.24, 96.25, 96.26; 128/4, 5, 6; 356/241

[56] References Cited

U.S. PATENT DOCUMENTS

| | | | |
|---|---|---|---|
| 1,726,268 | 8/1929 | Jahr | 128/7 |
| 2,002,595 | 5/1935 | Wappler | 128/7 |
| 2,793,639 | 5/1957 | Roberge | 128/6 |
| 2,987,960 | 6/1961 | Sheldon | 350/506 |
| 3,075,516 | 1/1963 | Strauch | 128/6 |
| 3,096,756 | 7/1963 | Rosenfeld et al. | 128/6 |
| 3,270,641 | 9/1966 | Gosselin | 128/4 |
| 3,614,891 | 10/1971 | Nolte | 356/241 |
| 3,773,039 | 11/1973 | Mori et al. | 128/6 |
| 3,804,081 | 4/1974 | Kinoshita et al. | 128/6 |
| 3,817,631 | 6/1974 | Kawahara | 128/6 |
| 3,856,000 | 12/1974 | Chikama | 128/6 |
| 3,880,148 | 4/1975 | Kanehira et al. | 128/6 |
| 3,889,662 | 6/1975 | Mitsui | 128/6 |
| 3,918,438 | 11/1975 | Hazamizer et al. | 175/110 |
| 4,078,555 | 3/1978 | Takahashi | 128/6 |
| 4,277,168 | 7/1981 | Oku | 350/96.26 |
| 4,286,585 | 9/1981 | Ogawa | 128/6 |
| 4,292,961 | 10/1981 | Kawashima | 128/6 |
| 4,383,761 | 5/1983 | Jones | 356/241 |
| 4,442,842 | 4/1984 | Baba | 128/6 |
| 4,530,568 | 7/1985 | Haduch et al. | 350/96.26 |
| 4,557,598 | 12/1985 | Ono et al. | 356/241 |

FOREIGN PATENT DOCUMENTS

| | | | |
|---|---|---|---|
| 10141 | 1/1985 | Japan | 356/241 |
| 178422 | 9/1985 | Japan | 350/96.26 |
| 880,639 | 10/1961 | United Kingdom | |
| 1296534 | 11/1972 | United Kingdom | |

OTHER PUBLICATIONS

Pulfer, CEGB Tech. Discl. Bull., No. 253, Sep. 1975, "Television Techniques fo Reactor Inspection," 3 pages.

Primary Examiner—William L. Sikes
Assistant Examiner—Frank González
Attorney, Agent, or Firm—Perman & Green

[57] ABSTRACT

An elongated, tubular inspection instrument characterized as having a control head at its proximal end and an objective assembly at its distal end. Flexible fiber or rigid optics extend between the control head and the objective assembly for the purpose of transmitting to the control head an image viewed from the distal end. Optics located at the objective assembly can be manipulated at the control head to provide, rapidly in succession, either a forward looking view or a sideward looking view. The sideward looking view is always at a positively positioned predetermined angle from the forward looking view.

28 Claims, 11 Drawing Figures

MULTIDIRECTIONAL VIEWING BORESCOPE

BACKGROUND OF THE INVENTION

I. Field of the Invention

The present invention relates to a borescope or endoscope utilizing flexible optical fibers or rigid optical systems for observation of the inside of the body cavities or of pipes and tubes in industrial applications. Throughout this disclosure, the term "borescope" will be used in a collective sense to include the entire range of elongated flexible and rigid optical inspection systems, endoscopes, sigmoidoscopes, and the like, whether intended for medical or industrial applications or for some other purpose.

II. Description of the Prior Art

Borescopes are commonly used for inspection of the human colon and urethra, and specifically, have been conventionally used in the diagnosis of tumors and other conditions in the lower gastrointestinal tract. The borescope examination involves the physician observing the intestinal wall through an eyepiece in the control head of the instrument. Generally, the borescope is provided with a source of illumination at its objective end, the end which is placed adjacent the area to be examined, and a bundle of light-transmitting fibers through which an image of the examined area is transmitted back to the eyepiece. The borescope can further incorporate a channel which provides a washing fluid for application to the site under examination as well as a surgical tip and other features.

Borescopes now available for medical purposes are also employed for observing the inside of a stomach, esophagus, and the like and can be classified into two typical types. One is the forward viewing type for observation along the longitudinal axis of the instrument at the distal end of the borescope and the other is the side viewing type for observation in one direction which is at a right angle or at some other angle relative to a longitudinal axis of the instrument at its distal end.

These two types have advantages and disadvantages, respectively. For example, in a narrow tubular region such as the esophagus, it is sometimes very difficult to use the side viewing type borescope because the site for observation is narrow and, moreover, it is difficult to provide a sufficient optical length between the lens and the object being inspected. Also, with a side viewing only type of borescope, one cannot see where one is transversing (that is, one cannot see in the same direction one is moving). Therefore, in such narrow tubular positions, forward-viewing type borescopes are generally used. On the other hand, in a wide bag-like cavity such a stomach, side viewing type borescopes are generally used because it is possible to observe all over the side walls.

For such reasons, the side viewing type borescope and the forward viewing type borescope are used for different applications according to the characteristics of the portion to be observed so that their respective advantages can be fully utilized. For example, when it is required to observe the esophagus and stomach of one patient at the same time, it is necessary to use two borescopes for the above reason. That is, the forward viewing type borescope is inserted for observing the esophagus at first and, after that, it is withdrawn and the side-viewing type borescope is inserted for observing the stomach. As a result, it takes a long time for observation. Moreover, as is widely known, pain of the patient is extremely pronounced when the hard distal end of the borescope passes his throat. Therefore, it is not desirable to insert two different borescopes successively because the pain of the patient will be further increased.

A factor to be considered in the construction of the borescope for its normal medical use is its flexibility and articulation which permits the objective tip to be directed along the channel of the colon, for example. A borescope can be made to traverse a considerable distance within the colon providing that any bends in the colon have a sufficiently large radius of curvature to enable the objective end of the borescope to be readily articulated to follow the course of the colon. Care must be taken, however, to precisely guide the instrument so as not to puncture the colon wall, especially as the device is being inserted.

Elongated tubular inspection devices, particularly such devices incorporating flexible fiber optics, are often used to inspect sites other than the internal organs of the human body which would not normally be visible to the human eye. The jet engine is one type of mechanical structure for which such inspection would be most useful, particularly, to inspect the first stage, or high temperature stage, of the engine just behind the burner can which has components that are most subject to wear and deterioration. The arrangement of the jet engine's rotor and stator blades, particularly those in the high temperature stage of the engine, presents a most complex geometry which has not been amenable to inspection in the past other than by first disassembling the engine. There has been a need for some form of inspection device which can be placed near the rotor and stator blades, and other important sites within the engine, for the inspection thereof without the laborious task of disabling the engine. The use of this type of instrument would effect a substantial savings in the cost of maintenance of the engines. Economy would result from the man-hours saved by avoiding the disassembly and reassembly of the engine. Additional economy would result from the increase in service time of the engine since the down time for maintenance would be substantially reduced.

While a jet engine has substantial regions of narrow channels and closed in spaces of the nature of the human colon or esophagus, it has an interior characterized by relatively open spaces more nearly of the nature of the human stomach. Hence it is most desirable for an industrial inspection system, as well as a medical inspection system, to have both forward viewing and side viewing capability. It would also be desirable for the system to be able to achieve this transition without time delay and without need for excessive manipulation of the system.

Although such devices currently exist, they are generally of a complex construction. This fact results, in a high initial cost plus substantial on-going expenses caused by the need for continuous maintenance. Also, some devices with interchangeable parts increase the probability of lost parts within the areas being viewed. It was with knowledge of the current state of the art that the present invention was conceived and has now been reduced to practice.

SUMMARY OF THE INVENTION

To this end, the present invention is directed toward an elongated, flexible, tubular inspection instrument characterized as having a control head at its proximal end and an objective assembly at its distal end. Fiber optics extend between the control head and the objective assembly for the purpose of transmitting to the control head an image viewed from the distal end. Appropriate optics located at the objective assembly include an image conversion means which can be manipulated at the control head to provide, rapidly in succession, either a forward looking view or a sideward looking or lateral view. The sideward looking view is always at a positively positioned predetermined angle from the forward looking view, and vice versa.

Therefore, a principal feature of the present invention resides in its capability of changing the observing direction, at any time, at the will of the operator, by providing a reflecting member rotatably mounted at the distal end, and on the object side of, the inspection instrument.

Another feature of the present invention resides in the ability of the inspection instrument to selectively change the observing direction by providing a rotatable reflecting member at the distal end for providing optical illumination as well as a reflecting member for the optical observation system such that both reflecting members are rotated in a unitary fashion.

Still another feature of the present invention resides in the ability of the inspection instrument to utilize a fiber optical bundle in a most efficient manner so as to permit the largest diameter possible of a bundle in keeping with the diameter of the instrument system.

Still another feature of the invention resides in its various fail safe expedients which assure the integrity of those parts of the system which are inside a cavity to be inspected.

Other and further features, objects, advantages, and benefits of the invention will become apparent from the following description taken in conjunction with the following drawings. It is to be understood that both the foregoing general description and the following detailed description are exemplary and explanatory but are not restrictive of the invention. The accompanying drawings which are incorporated in and constitute a part of this invention, illustrate some of the embodiments of the invention and, together with the description, serve to explain the principles of the invention in general terms.

DESCRIPTION OF THE PREFERRED EMBODIMENT

Figure 1:
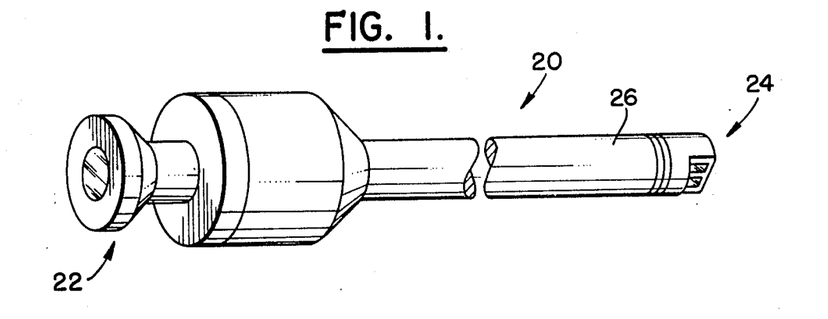
FIG. 1 is an overall perspective view of an inspection instrument embodying the present invention.

Turn now to the drawings and initially to FIG. 1 which illustrates a borescope 20 embodying the invention. The borescope 20 comprises a control head 22 at a proximal end of the instrument and an objective head 24 at a distal end of the instrument. A flexible sheath 26, preferably of the thin walled noncorrosive metal, connects the control head to the objective head and envelopes those operating components of the instrument which extend between the control head and the objective head as will be described below.

Figure 2:
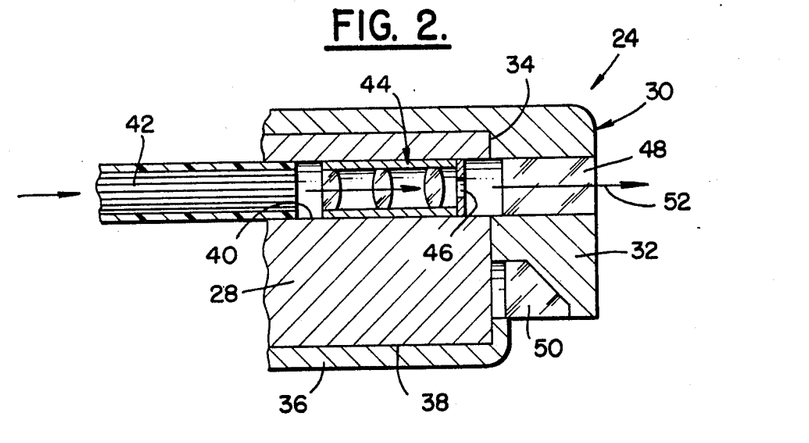
FIG. 2 is a diagrammatic cross section view of the objective assembly at the distal end of the instrument illustrated in FIG. 1 illustrating the relative positioning of parts to obtain a direct view of an object being examined.

As illustrated in FIG. 2, the objective assembly 24 includes an objective head 28 which is bonded to a distal end of the sheath 26 in a suitable manner and a rotary head 30 which is rotatably mounted on the objective head at an end distant from the control head 22. The rotary head 30, in turn, includes a cap member 32 positioned immediately adjacent an end wall 34 of the objective head 28 and a cylindrical skirt 36 which projects away from the cap member end slidingly engages a similarly shaped outer surface 38 of the objective head 28. A longitudinally extending bore 40 receives a distal end of a fiber optic bundle 42 which is bonded in place in the bore. Also suitably mounted in the bore is a lens cell 44 aligned with the fiber optic bundle to provide, in cooperation with a suitable aperture 46, an image on an end of the bundle 42 for transmission back to the control head 22.

Figure 3:
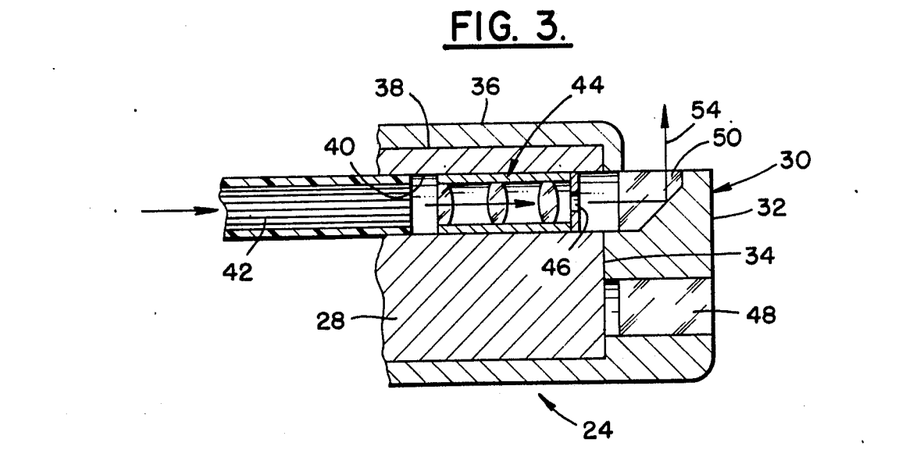
FIG. 3 is a diagrammatic cross section view, similar to FIG. 2, illustrating another relative positioning of the parts to obtain a side view of the object being examined.

The cap member 32 is suitably formed to integrally receive a plano lens 48 and an image reflecting member 50 which may be, for example, a prism or a mirror. The lens 48 and the reflecting member 50 are positioned at diametrically opposite locations about a longitudinal axis of the objective head 28 and the rotary head 30. Thus, in one position as seen in FIG. 2, the plano lens 48 is aligned with the fiber optic bundle 42, the lens cell 44, and the aperture 46. In this manner, the borescope 20 enables an operator to make observations downstream of itself along a view path as generally indicated by an arrow 52. However, with minimal effort in a manner to be described, an operator of the borescope 20 can reposition the rotary head 30 so that it assumes the position illustrated in FIG. 3. In that position, the image reflecting member 50 is aligned with the fiber optic bundle 42, lens cell 44, and aperture 46 enabling an operator to make observations in a lateral, or other than forward looking, direction or view path as represented by an arrow 54.

Figure 4:
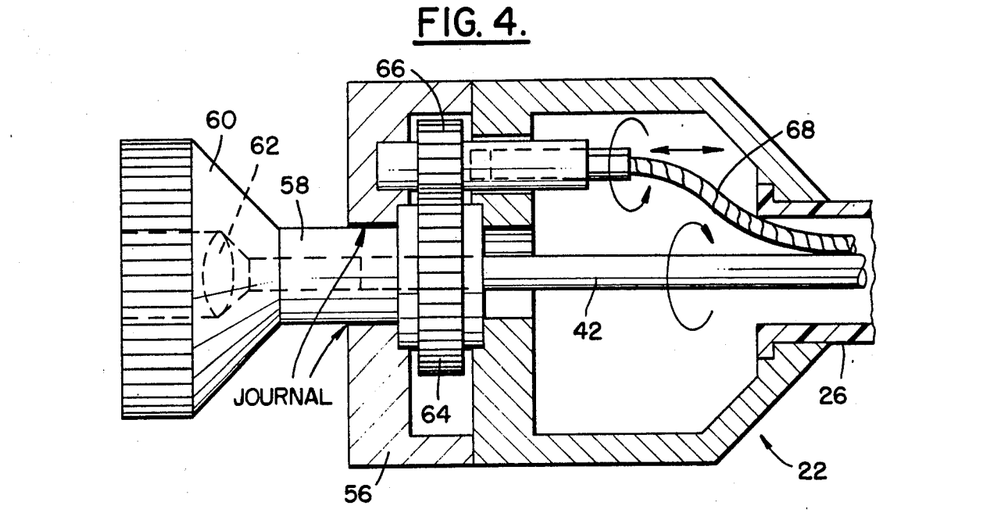
FIG. 4 is a detail side elevation view, partially in cross section of the control head at the proximal end of the instrument illustrated in FIG. 1.

As noted above, the motions just described occurring at the objective assembly 24 take place when an operator imparts motion to the system at the control head 22. Details of the construction of the control head 22 are illustrated in FIG. 4. The control head 22 includes a housing 56 in which is journaled a turnbuckle 58 for rotation about a longitudinal axis. An eyepiece 60 is suitably fixed to the turnbuckle 58 and includes a lens 62 which serves to bring into focus for the eye of the operator an image appearing at a proximal end of the fiber optic bundle 42. The bundle 42 is received in a longitudinal bore formed in the turnbuckle 58 and fixed thereto in a suitable fashion. A spur gear 64 is fixed to an end of the turnbuckle 58 opposite the eyepiece 60 and is drivingly engaged with a pinion gear 66 rotatably supported on the housing 56. A proximal end of a flexible shaft 68 is engaged with the spur gear 64 for rotation therewith.

Figure 5:
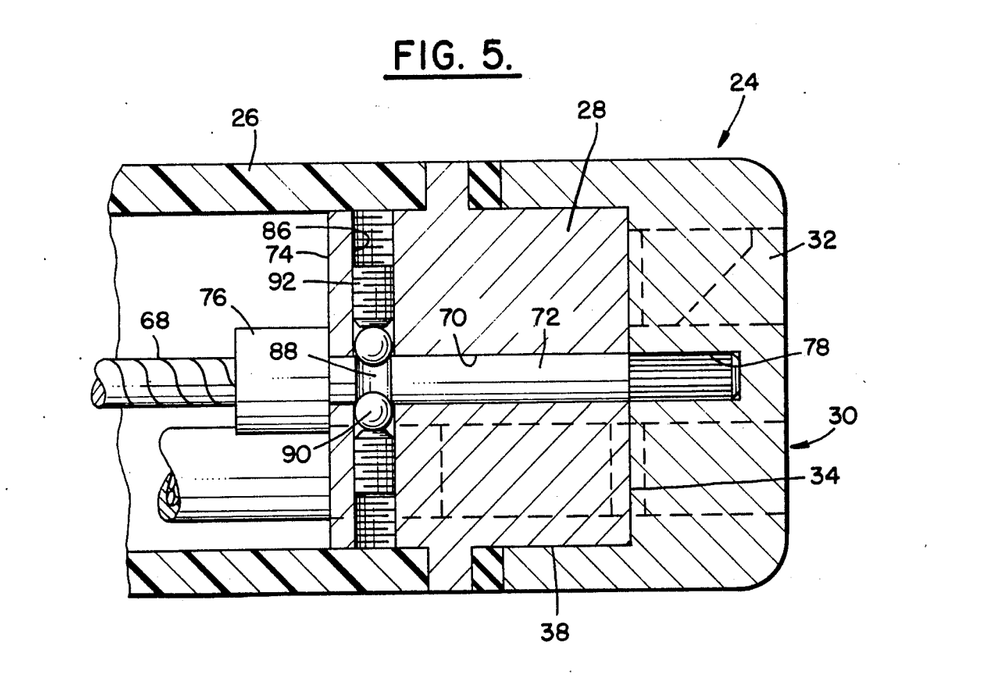
FIG. 5 is a side elevation view in section, similar to FIGS. 2 and 3, but illustrating in greater detail the construction of the distal end of the instrument illustrated in FIG. 1.

At the distal end of the borescope 20 as seen in FIG. 5, the objective head 28 which has an outer contour generally of a right cylinder is provided with a central bore 70 aligned with its central axis. The central bore 70 slidably receives a rigid shaft 72 which extends beyond the endwall 34 on the far side of the objective head and beyond an endwall 74 at a near side of the objective head 28. At its near end, the shaft 72 is rigidly attached to a distal end of the flexible shaft 68 by means of a suitable coupling 76. At its far end, the shaft 72 is fittingly received in a bore 78 formed in the cap member 32 coextensive with a central axis of the rotary head 30. It will be appreciated, as particularly well seen in FIG. 6, that, like the objective head 28, the rotary head 30 is also of a cylindrical shape, closely conforming to that of the objective head 28. In addition to the fitting reception of the end of the shaft 72 in the bore 78, a suitable adhesive may be employed to assure integrity therebetween.

Figure 6:
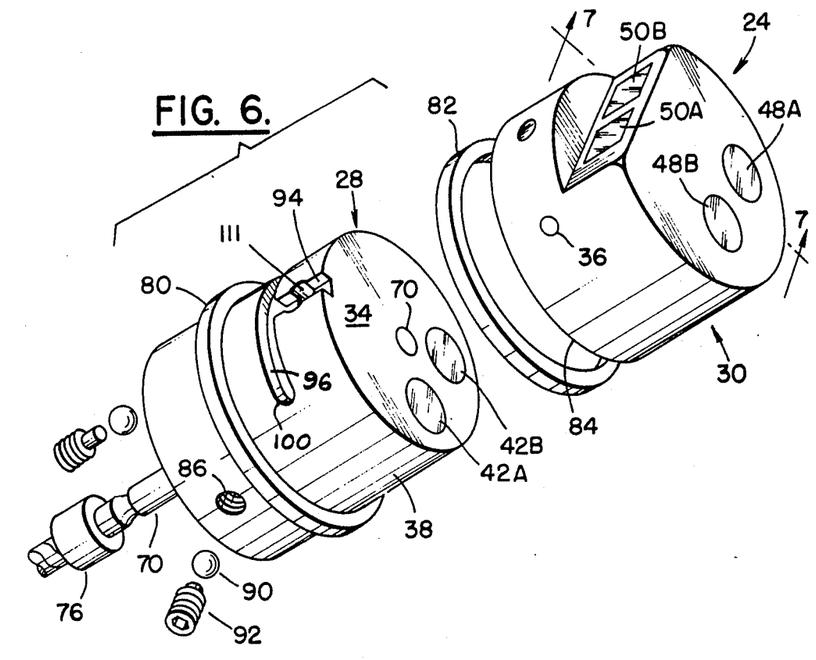
FIG. 6 is an exploded perspective view illustrating components located at the distal end of the instrument.

It is also noteworthy, viewing FIG. 6, that the objective head 28 is provided with an integral annular band 80. A suitable gasket 82 surrounds the outer surface 38 adjacent the annular band 80 and an extreme rim 84 of the skirt 36. The gasket 82 serves to prevent the intrusion of contaminants into the interior of the objective assembly 24.

With continued reference to FIG. 5, it can be seen that the objective head 28 is provided with a pair of threaded radial bores 86, although one would be adequate for the purpose about to be described. Each threaded bore 86 is aligned with an annular groove 88 formed in the shaft 72. During assembly, after the shaft has been located within the central bore 70, a ball 90 is inserted into each bore 86 so that it engages the annular groove 88. Thereafter, a set screw 92 threadedly received in the bore 86 is tightened against the ball to an extent which permits rotation of the shaft but prevents axial movement of the shaft relative to the objective head 28. This construction, then, provides one fail safe expedient to prevent loss of any component from the distal end of the borescope 20 into the cavity being examined.

With the construction described to this point, it is readily apparent that the operator of the borescope can, by turning the turnbuckle 38 at the control head 22, rotate the flexible shaft 68 via the gears 64 and 66 and, in turn, the rotary head 30 at the distal end of the borescope 20. As can be seen in FIG. 6, it is desirable that there be a pair of fiber optic bundles, specifically represented by reference numerals 42A and 42B. According to this arrangement, bundle 42A is connected at its proximal end to a high intensity light source and serves to provide illumination at the distal end of the borescope 20. The bundle 42B serves to project the image of the object being viewed back to the control head 22. Similarly, the rotary head 30 is provided with a pair of plano lenses 48A and 48B which cooperate in the manner previously described in the discussions of FIGS. 2 and 3, with the light bundles 42A and 42B, respectively. In a similar fashion, the rotary head 30 is also provided with a pair of image reflecting members 50A and 50B which also cooperate with the bundles 42A and 42B, respectively, for sideways viewing as previously described with respect to FIGS. 2 and 3.

Figure 7:
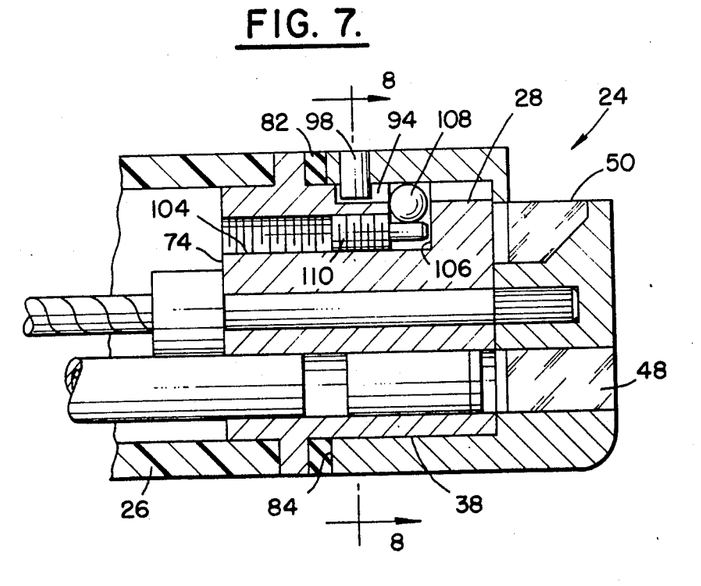
FIG. 7 is a detail cross section view taken generally along line 7—7 in FIG. 6.

With particular reference to FIGS. 6 and 7, it is readily seen how the objective assembly is put together. The objective head 28 is formed with a longitudinally extending access track 94 cut into the outer surface 38 thereof. The access track 94 leads into an arcuate track 96 also cut into the outer surface 38 and lying in a plane perpendicular to an axis of the objective head 30 or generally parallel with the plane of the endwall 34. The track 96 extends for approximately 180° around the circumference of the objective head. A guide pin 98 is fixed to an inner surface of the rotary head 30 (FIGS. 7 and 8) and extends radially inwardly to an extent such that it is receivable within the track 94 but would prevent placement of the rotary head on the objective head in any other orientation. As the rotary head 30 is mounted on the objective head 28, the guide pin 98 slides along the access track 94 until it reaches the arcuate track 96. As this occurs, the rim 84 sealingly engages the gasket 82. The rotary head is then free to rotate on its axis with the guide pin 98 following along the track 96 between its terminal regions denoted as index stops 100 and 102 as most clearly seen in FIG. 8.

Figure 8:
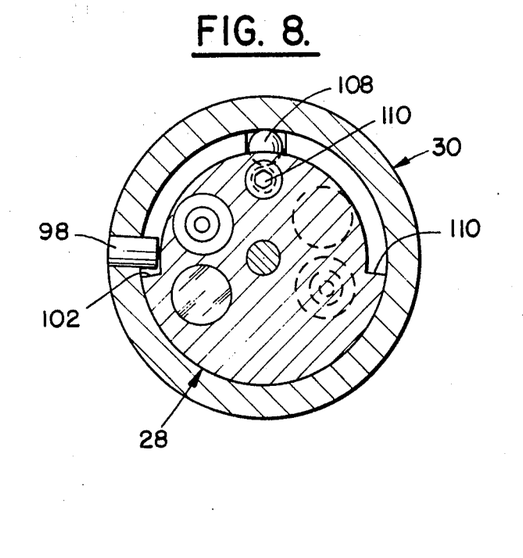
FIG. 8 is a diagrammatic section view taken generally along line 8—8 in FIG. 7.

When the guide pin 98 engages the index stop 100, the rotary head 30 is so oriented that an operator at the control head 22 has a forward looking view of the object being examined. Similarly, when the rotary head 30 is rotated to the point that the guide pin 98 engages the index stop 102, the operator is afforded a side looking view of the object being examined. Thus, the borescope 20 permits, in rapid succession, both forward observation along the view path 52 (FIG. 2) and sideways observation along the view path 54 (FIG. 3), such as at a 90° angle to the forward observation, each being achieved at an extremity of travel of the rotary head 30. This means that the operator need only rotate the turnbuckle 58 to an extreme position in one direction in order to achieve a forward view of the object being examined, then rotate the turnbuckle 58 in the opposite direction to an extreme position in order to obtain a side view of the object being examined. Thus, the operator need not be concerned with fine adjustments or other time consuming operations.

Another, or second, fail safe expedient to assure the integrity of the objective assembly 24 within the cavity being examined resides in the relative positioning of the guide pin 98 and the arcuate track 96. By reason of this design, the rotary head 30 cannot be withdrawn from the objective head 28 so long as the guide pin 98 engages a sidewall of the track 96.

Yet another, or third, fail safe expedient is provided for the instance in which the guide pin 98 is aligned with the access track 94 as it travels between the index stops 100 and 102. Thus, it has seen in FIG. 7, a longitudinal threaded bore 104 is formed in the objective head 28 and connects to a stub radial bore 106. With the rotary head 30 positioned on the objective head 28, a ball 108 having a diameter only slightly less than that of the bores 104 and 106 is inserted from the end wall 74 followed by a set screw 110. As seen in FIG. 8, the set screw 110 holds the ball 108 in position at an enlarged region 111 (FIG. 6) of the access track 94 engaging an inner surface of the rotary head 30 and generally extending across the access track 94. With the ball 108 so positioned, it acts as a barrier to prevent withdrawal of the guide pin 98 along the access track 94 thereby further assuring the integrity of the objective assembly 24 within the cavity being examined.

Figure 9:
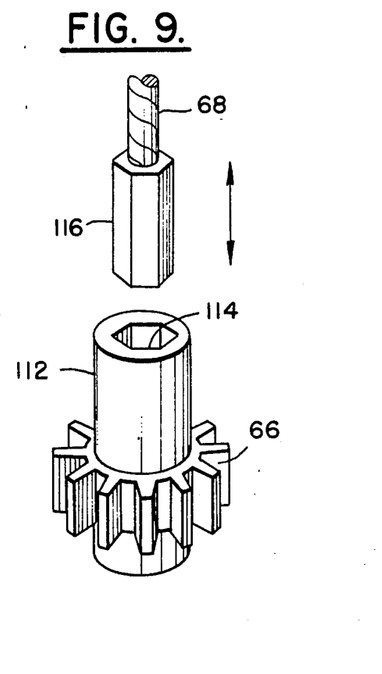
FIG. 9 is a detail exploded view of selected parts located at the proximal end of the instrument of the invention.

Turning now to FIG. 9, it is seen that the pinion gear 66 at the proximal end of the borescope 20 is provided with a substantial boss 112 provided with a non-round bore 114 which serves to slidingly receive a similarly formed fitting 116 fixed at a proximal end of the flexible shaft 68. A connection between the bore 114 and the fitting of 116 is such as to assure that rotation of the gear 66 is imparted to the shaft 68 while permitting sliding motion between the boss 112 and the fitting 116. Such a result can be achieved by splining, by keying or by using cross sectional shapes that are other than round. The purpose of this construction is to accommodate the need to lengthen the shaft 68 as the borescope 20 becomes convoluted, while assuring that rotation of the turnbuckle 58 at the control head 22 is imparted to the rotary head 30. It will also be appreciated in this context that according to a preferred construction, the pinion gear 66 is much smaller than the spur gear 64. Because of this construction, twisting of the cable is controllable and, in any event, is accounted for in the operation of the instrument.

It will also be appreciated that although a flexible shaft has been illustrated and described as being the means by which motion imparted at the turnbuckle 58 is transmitted to the rotary head 30, there may be applications in which a rigid shaft would be more desirable. It is also contemplated that the control could be by way of a cam arrangement, or by electric motors, or by electromagnets suitably positioned and operated within the objective assembly. Additionally, a rigid optical system may be employed rather than the flexible fiber optics which have heretofore been discussed.

Figure 10:
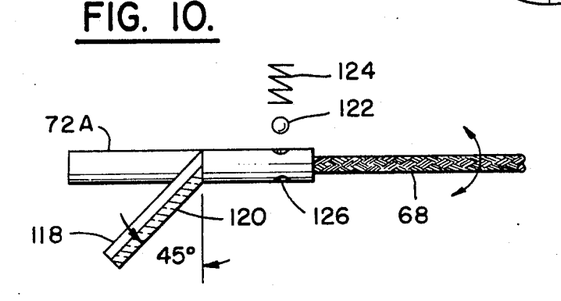
FIG. 10 is a detail side elevation view of another embodiment of the invention.

It is also within the scope of the invention to provide a construction somewhat different from the image reflecting member 50 already described. With reference to FIG. 10, it might be desirable to suitably mount to a modified shaft 72, here indicated by a reference numeral 72A, an angularly disposed plate 118 to which is suitably bonded or formed a mirrored surface 120. The mirrored surface could be inclined at a 45° angle, or some other desired angle, with relation to the longitudinal axis of the shaft 72A. Also, sufficient material, in this embodiment, would be removed from the objective 78 head to allow for movement of the plate 118 and its mirrored surface 120 upon rotation of the shaft 72A.

In this embodiment, there would be no need for the reflecting member 50 nor would the rotary head 30 be rotatably mounted on the objective head 28 but would be fixed thereon. When the operator, utilizing this embodiment, desires to achieve a forward view of the object being examined, the shaft 68 is rotated to a position at which the plate 118 is out of line with the fiber optic bundle 42. However, when the operator desires to obtain a side view of the object being examined, the shaft 68 is rotated to a position at which the mirrored surface 120 is aligned with the fiber optic bundle 42. Of course, the head 30 would require a side window (not shown) coextensive with the plate 118 to assure the workability of this embodiment. To further assure the positioning of the mirrored surface 120, it might be desirable to employ a locating mechanism such as a ball 122 biased by a spring 124 into a detent 126 of the shaft 72A as can be done in a well known manner.

Figure 11:
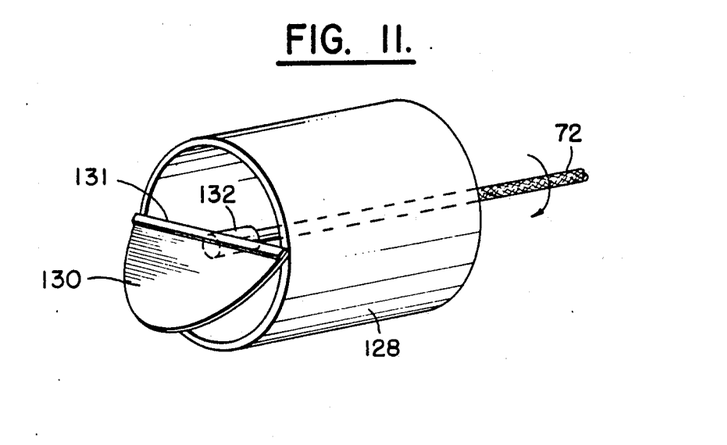
FIG. 11 is a detail perspective view of yet another embodiment of the invention.

Still another embodiment of the invention is illustrated in FIG. 11. According to this embodiment, a bushing 128 having an outer diameter which is generally equivalent to that of the objective head 128 is inserted between the objective head 28 and the rotary head 30 and is coaxial therewith. The bushing 128 is cylindrical in shape and has a flap 130 extending forwardly away from a distal end thereof, strengthened by a diametrically extending brace 131 fixed to the sidewalls of the bushing 128 at its distal end. As with the plate 118, the flap 130 is also provided with a mirrored surface. By means of an appropriate fitting 132, the shaft 72 rotates the bushing 128 on its axis so as to rotate the flap 130 either into alignment with the fiber optic bundle 42 or out of alignment therefrom according to the desires of the operator.

Other modifications to the details of the concept and apparatus disclosed herein are also possible. For instance, the side looking view could be any convenient or desired angle such as 30°, 60°, etc. relative to the forward looking view. In addition, with some modification to the construction of the rotary head, several side looking views are possible, look at a different angle relative to the forward looking view. In this case, the rotary head would have to have a different reflecting mirror for each side looking angle desired as well as coordinated index stop means therefor.

While the preferred embodiment of the invention has been disclosed in detail, it should be understood by those skilled in the art that various modifications may be made to the illustrated embodiment without departing from the scope as described in the specification and defined in the appended claims.

We claim:

1. An elongated tubular inspection instrument having a longitudinal axis and a control head at a proximal end thereof and an objective assembly at the distal end thereof for viewing an object to be inspected comprising:
   optic means located between said control head and said objective assembly for transmitting an image from said distal end to said control head; and
   said objective assembly including:
   an objective head for supporting a distal end of said optic means; and
   image conversion means rotatably mounted on said objective head about the longitudinal axis at an end distant from said control head for movement between first and second positions, said image conversion means including an image reflecting member and forward viewing means which are relatively fixed such that in said first position, said optic means is aligned with said forward viewing means and has an unhampered forward view whereby an image is received at said control head of an object positioned beyond said objective assembly, and such that in said second position, said image reflecting member is aligned with said optic means whereby an image is received at said control head of an object positioned laterally of said objective assembly; and
   said image conversion means being ineffective to transmit an image to said control head when positioned intermediate said first and second positions.

2. An inspection instrument as set forth in claim 1 wherein said optic means is a flexible fiber optic system.

3. An inspection instrument as set forth in claim 1 wherein said optic means is a rigid optical system.

4. An inspection instrument as set forth in claim 1 wherein said objective head has at least one bore extending therethrough in an axial direction adapted to fixedly receive the distal end of said optic means.

5. An inspection instrument as set forth in claim 4 wherein said objective head has a longitudinal axis; wherein the bore is radially offset from the longitudinal axis of said objective head; wherein said image conversion means includes; a rotary head having a longitudinal axis aligned with that of said objective head and rotatably mounted thereon; and a plano lens mounted on said rotary head offset from the axis thereof; and a reflecting member mounted on said rotary head offset from the axis thereof; said plano lens and said reflecting member positioned at radial distances from the axis of said plane lens equal to that of the bore from the axis of said objective head; and said plano lens and said reflecting member being at azimuthally spaced locations on said rotary head.

6. An inspection instrument as set forth in claim 1 wherein said objective assembly includes a seal between said objective head and said image conversion means to isolate the interior thereof from contaminants.

7. An inspection instrument as set forth in claim 1 wherein said image conversion means is movable on said objective head between defined limits, said objective head including: an indexing stop member which abuts said image conversion means when said image conversion means respectively reaches said first and second positions.

8. An inspection instrument as set forth in claim 1 wherein said objective head has a cylindrical outer peripheral surface with a circumferentially extending slot therein having first and second terminal regions; and wherein said image conversion means has a cylindrical skirt slidingly received on said outer peripheral surface of said objective head; and wherein said image conversion means includes a radially inwardly extending indexing pin slidably received in the slot, said rotary head being movable on said objective head between said first position whereat said indexing pin abuts said first terminal region and said second position whereat said indexing pin abuts said second terminal region.

9. An inspection instrument as set forth in claim 8 wherein said cylindrical skirt has a continuous rim at an extremity thereof and a longitudinally extending slot therein extending from said rim to the circumferentially extending slot to slidably receive said pin when initially mounting said image conversion means onto said objective head and including barrier means on said objective head extending into the longitudinal slot and engageable with said skirt to prevent removal of said image conversion means from said objective head.

10. An inspection instrument as set forth in claim 1 wherein said objective head includes: a lens cell mounted adjacent said distal end of said fiber optic means for focusing an image onto said distal end of fiber optic means.

11. An inspection instrument as set forth in claim 1 wherein said image reflecting member is a mirror.

12. An inspection instrument as set forth in claim 1 wherein said image reflecting member is a prism.

13. An inspection instrument as set forth in claim 1 wherein said control head includes: operating means; and wherein said instrument includes drive means intermediate said operating means and said objective assembly; whereby said operating means is effective to rotate said image conversion means between said first and second positions.

14. An inspection instrument as set forth in claim 13 wherein said control head includes: a housing; wherein said operating means is rotatably mounted on said housing; and wherein said drive means includes: a drive gear fixed on said operating means for rotation therewith; a pinion rotatably mounted on said housing drivingly engaged with said drive gear; and drive shaft means rotatably fixed at one end to said pinion and at its opposite end to said rotary head.

15. An inspection instrument as set forth in claim 14 wherein said objective head and said image conversion means each has a central axially directed bore therein, such central bores being axially aligned; and wherein said drive means includes: rotatably mounted flexible means, one end of said flexible means being fittingly received in the central bore of said image conversion means, an opposite end of said flexible means extending to said control head; and whereby rotation of said operating means causes rotation of said image conversion means between said first and second positions.

16. An inspection instrument as set forth in claim 14 including: a flexible sheath enveloping said optic means and said drive shaft means and extending between said control head and said objective assembly, one end of said sheath being bonded to said housing, the other end of said sheath being bonded to said objective head.

17. An inspection instrument as set forth in claim 14 wherein: said pinion has an outwardly extending boss thereon with a non-round axial bore therein; and wherein: said one end of said drive shaft means has an enlarged end slidably received in the axial bore but rotatable therewith; so as to accommodate extensions of said drive shaft means which occur when said instrument is caused to bend.

18. An inspection instrument as set forth in claim 15 including removal preventing means on said objective head for preventing inadvertent removal of said shaft means from said objective head.

19. An inspection instrument as set forth in claim 18 wherein said rigid shaft has an annular groove therein; and wherein said objective head has a radial bore therein terminating at said groove; said removal preventing means including: a ball received in the radial bore and engaging said groove; and a set screw threadedly engaged with the radial bore adjacent the central bore such that when said set screw is tightened, it engages said ball and thereby prevents axial movement of said rigid shaft relative to said objective head.

20. An inspection instrument as set forth in claim 1 wherein said optic means is a fiber optic system including a first bundle for illuminating the region external of said distal end of said instrument and a second bundle for transmitting an image from said distal end to said control head.

21. An inspection instrument as set forth in claim 1 wherein said image conversion means includes:
   a shaft mounted on said objective head and rotatable between said first and second positions;
   a plate fixed on said shaft, said plate being angularly disposed relative to a longitudinal axis of said shaft and extending away from said shaft with increasing distance from said proximal end; and
   a reflecting surface on said plate.

22. An inspection instrument as set forth in claim 21 including detent means mounted on said objective head and engageable with said shaft for locating, respectively, said first and second positions.

23. An inspection instrument as set forth in claim 1 wherein said image conversion means includes:
   a cylindrical bushing member having a longitudinal axis aligned with that of said objective head and open at both ends;
   a diametrically extending brace having opposed ends fixed to said bushing at one opening of said bushing distant from said proximal end;
   a fitting fixed to said brace and rotatably mounted on said objective head on the axis thereof;
   a flap fixed to said brace, said flap being angularly disposed relative to a longitudinal axis of said bushing and extending away from said shaft with increasing distance from said proximal end; and
   a reflecting surface on said plate.

24. An endoscope type instrument having proximal and distal ends thereof and having a longitudinal axis, said instrument comprising:
   a control head at the proximal end of said instrument;
   an objective head at the distal end of said instrument;
   optic means located between said control head and said objective head for transmitting an image from said distal end to said control head for viewing an object to be inspected, said objective head supporting a distal end of said optic means;
   image conversion means for selective viewing in one of only two distinct directions, a first direction through a first view path and a second direction through a second view path;
   means for mounting said image conversion means to said objective head for rotation about the longitudinal axis so as to selectively enable each of said first and second view paths in said image conversion means to be moved, respectively, to a location adjacent said distal end of said optic means on said objective head beyond said objective head; and
   said control head including means for selecting one of said directions to be viewed in response to which said image conversion means is positioned so that a selected one of said first and second view paths is located adjacent said distal end of said optic means for viewing in said associated direction and a resultant image is received by the distal end of said optic means and transmitted to said control head.

25. An instrument as set forth in claim 24 wherein said objective head has at least one bore extending therethrough in an axial direction adapted to fixedly receive the distal end of said optic means;
   wherein said objective head has a longitudinal axis;
   wherein the bore is radially offset from the longitudinal axis of said objective head;
   wherein said image conversion means includes;
   a rotary head having a longitudinal axis aligned with that of said objective head and rotatably mounted thereon; and
   an image conversion optical system mounted on said rotary head offset from the axis thereof; and
   a reflecting member mounted on said rotary head offset from the axis thereof;
   said image conversion optical system and said reflecting member positioned at radial distances from the axis of said optic means equal to that of the bore from the axis of said objective head; and
   said image conversion optical system and said reflecting member being at azimuthally spaced locations on said rotary head.

26. An instrument as set forth in claim 24 further including a seal between said objective head and said image conversion means to isolate the interior thereof from contaiminants.

27. An instrument as set forth in claim 24 wherein said image conversion means is movable on said objective head between defined limits, said objective head including an indexing stop member which abuts said image conversion means when said image conversion means respectively reaches said first and second view paths.

28. An instrument as set forth in claim 24 wherein said control head includes operating means; and
   wherein said instrument includes drive means intermediate said operating means and said image conversion means whereby said operating means is effective to rotate said image conversion means between said first and second view paths.

* * * * *